United States Patent [19]

King

[11] Patent Number: 4,559,346

[45] Date of Patent: Dec. 17, 1985

[54] CERTAIN N-OCTAHYDRO-INDOLIZINEBENZA-MIDES AND THEIR USE IN TREATING PSYCHOSIS, CARDIAC ARRHYTHMIA AND HYPERTENSION

[75] Inventor: Francis D. King, Newport, England

[73] Assignee: Beecham Group p.l.c., Brentford, England

[21] Appl. No.: 487,904

[22] Filed: Apr. 22, 1983

[30] Foreign Application Priority Data

Apr. 23, 1982 [GB] United Kingdom ............... 8211882

[51] Int. Cl.$^4$ ............... A61K 31/445; C07D 471/04
[52] U.S. Cl. ............... 514/299; 514/309; 546/112; 546/143; 546/146; 546/150
[58] Field of Search ............... 546/112, 143, 146, 150; 424/256, 258; 514/299, 309

[56] References Cited

U.S. PATENT DOCUMENTS

4,391,978  7/1983  Imhof et al. ............... 546/138

FOREIGN PATENT DOCUMENTS

36269   9/1981  European Pat. Off. .
37990  10/1981  European Pat. Off. .
67565  12/1982  European Pat. Off. .
1593146  7/1981  United Kingdom .

OTHER PUBLICATIONS

I. Claxton et al., "BRL 8242 (2-[2-Benzimidazolyl-]-Amino-2-Imidazoline Dihydrochloride), A New Inhibitor of Dopamine-β-Hydroxylase with Antihypertensive Activity", *European Journal of Pharmacology*, 37 (1976) 179-188.

G. Poulain, "Synthese des nitriles-aldehydes succinques α,α-disubstitues et transformation de ceux-ci en diacides, nitriles-acides et imides correspondants", *Bull. Soc. Chim. Fr.* 1964, 913.

P. Protais et al., "Climbing Behavior Induced by Apomorphine in Mice: A Simple Test for the Study of Dopamine Receptors in Striatum", *Psychopharmacology*, 50, 1-6 (1976).

Primary Examiner—Henry R. Jiles
Assistant Examiner—Bernard I. Dentz
Attorney, Agent, or Firm—James F. Haley, Jr.; Paul H. Ginsburg

[57] ABSTRACT

A compound of formula (I), or a pharmaceutically acceptable salt, N-oxide or solvent adduct thereof:

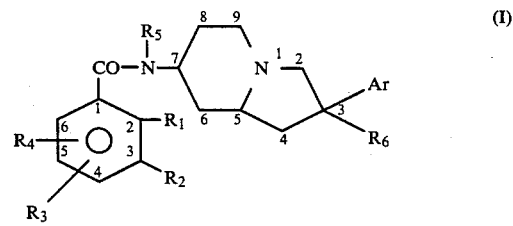

wherein:
R$_1$ is C$_{1-6}$alkoxy, C$_{1-6}$alkylthio or, together with R$_5$ is C$_{1-2}$alkylene, and one of R$_2$, R$_3$ and R$_4$ is hydrogen and the other two together are C$_{1-2}$ alkylenedioxy, or the other two are the same or different and are selected from the class of hydrogen, halogen, trifluoromethyl, C$_{1-6}$ alkyl, C$_{1-6}$ alkoxy, C$_{1-6}$ alkylthio, C$_{1-7}$acyl, C$_{1-7}$ acylamino, C$_{1-6}$alkylsulphonyl, C$_{1-6}$alkylsulphinyl hydroxy, nitro or amino, aminocarbonyl or aminosulphonyl optionally N-substituted by one or two C$_{1-6}$alkyl, C$_{3-8}$ cycloalkyl, phenyl or phen C$_{1-4}$alkyl groups or optionally N-disubstituted by C$_{4-5}$ polymethylene, or R$_1$ and R$_2$ together are C$_{1-2}$ alkylenedioxy, and R$_3$ and R$_4$ together are C$_{1-2}$ alkylenedioxy or R$_3$ and R$_4$ are the same or different and are selected from the previously defined class of substituents;
R$_5$ is hydrogen or as defined with R$_1$;
R$_6$ is hydrogen or C$_{1-6}$ alkyl; and
Ar is phenyl or thien-2-yl or thien-3-yl, optionally substituted by one or two groups, which are the same or different selected from C$_{1-4}$ alkoxy, trifluoromethyl, halogen, carboxy, esterified carboxy or C$_{1-4}$ alkyl optionally substituted by hydroxy, C$_{1-4}$alkoxy, carboxy, esterified carboxy or in vivo hydrolyzable C$_{1-4}$acyloxy; Ar being in the 3β configuration as defined in formula (VIII); and Ar may also have the α-configuration when one of R$_2$, R$_3$ and R$_4$ is hydrogen and the other two are independently selected from optionally substituted amino or aminosulphonyl as defined, C$_{1-6}$ alkylsulphonyl or C$_{1-6}$ alkylsulphinyl; or
R$_1$ and R$_2$ together are C$_{1-2}$ alkylenedioxy and R$_3$ and R$_4$ are independently selected from the same group of substituents, compositions thereof and processes therefor. The compounds are useful in the treatment of psychosis and hypertension for example.

17 Claims, No Drawings

CERTAIN N-OCTAHYDRO-INDOLIZINEBENZAMIDES AND THEIR USE IN TREATING PSYCHOSIS, CARDIAC ARRHYTHMIA AND HYPERTENSION

This invention relates to novel benzamides having useful pharmacological activity, to a process for their preparation, and to pharmaceutical compositions containing them.

U.K. Pat. No. 1593146 discloses benzamides of formula (A):

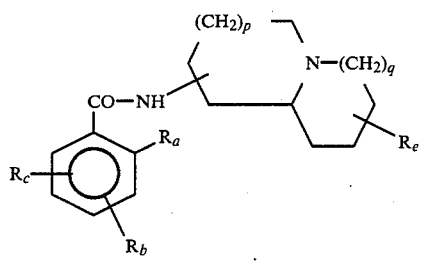

wherein:
$R_a$ is $C_{1-6}$ alkoxy;
$R_b$ and $R_c$ are the same or different and are hydrogen, halogen, $CF_3$ hydroxy, $C_{1-6}$alkoxy, $C_{2-7}$acyl, amino, amino substituted by one or two $C_{1-6}$alkyl groups, $C_{2-7}$acylamino, aminocarbonyl or aminosulphonyl optionally substituted by one or two $C_{1-6}$alkyl groups, $C_{1-6}$ alkysulphonyl or nitro;
p is 0 to 3;
q is 0 to 3; the amide and heterobicyclic nitrogen atoms are separated by at least two carbon atoms;
$R_d$ is hydrogen, $C_{1-6}$alkyl, phenyl or phenyl $C_{1-6}$alkyl, either of which phenyl moiety may be substituted by $C_{1-6}$alkyl, $C_{1-6}$alkoxy, $CF_3$ or halogen; and
$R_e$ is hydrogen or $R_d$ and $R_e$ are attached to two adjacent carbon atoms and form together with these two carbon atoms a fused benzene ring, which benzene ring may be substituted by $C_{1-6}$alkyl, $C_{1-6}$alkoxy, $CF_3$ or halogen. Such benzamides are described as being useful for the treatment of disorders of the gastro-intestinal function, such as retarded gastric emptying, dyspepsia, flatulence, oesophagal reflux, peptic ulcer and emesis.

Specific examples of compounds of formula (A) disclosed in the aforementioned UK patent include the compounds of examples 3 and 4, namely 4-acetylamino-5-chloro-2-methoxy-N-(7-octahydro-indolizinyl)benzamide and 4-amino-5-chloro-2-methoxy-N-(7-octahydro-indolizinyl)benzamide respectively.

European patent publication No. 37990 discloses in part benzamides of formula (B):

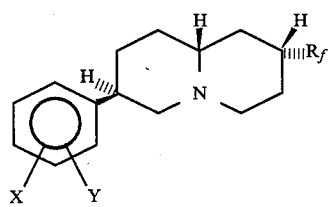

wherein:
X is hydrogen, fluoro, chloro, lower alkoxy, lower alkyl or trifluoromethyl;
Y is hydrogen, fluoro, chloro, lower alkoxy or lower alkyl; and
$R_f$ is inter alia acylamino. Such compounds are described as having neuroleptic, antiemetic and/or analgesic activity.

Included within the definition of acylamino for $R_f$ is benzoylamino optionally substituted by halogen, amino, lower alkoxy, sulphamoyl and/or lower alkylsulphonyl.

Specific examples of compounds of formula (B) disclosed in the aforementioned European patent publication include the compounds, 4-amino-5-chloro-N-[(9αβ)-7β-(o-chlorophenyl)-octahydro-2H-quinolizin-2α-yl]-o-anisamide (in racemic form), N-[(9αβ)-7β-(o-chlorophenyl)-octahydro-2H-quinolizin-2α-yl]-5-(ethylsulphonyl)-o-anisamide (in racemic form) and N-[(9αβ)-7β-(o-chlorophenyl)-octahydro-2H-quinolizin-2α-yl]-p-fluorobenzamide (in racemic form).

A novel class of indolizidinylbenzamides has now been discovered which contain an optionally substituted phenyl or thienyl substitution on the 5-membered ring of the indolizidinyl moiety. Such compounds are dopamine antagonists and generally have anti-emetic activity. In addition, they also have, depending on their balance between central and peripheral action on the nervous system, anti-psychotic activity and/or the ability to regulate the gastro-intestinal function.

Accordingly, the present invention provides a compound of formula (I), or a pharmaceutically acceptable salt or N-oxide thereof; or a solvate of any of the foregoing:

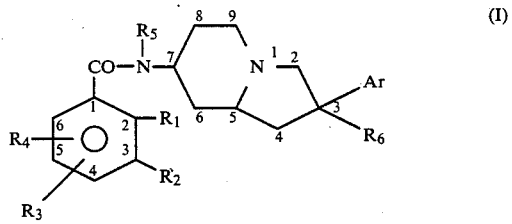

wherein:
$R_1$ is $C_{1-6}$alkoxy, $C_{1-6}$alkylthio or, together with $R_5$ is $C_{1-2}$alkylene, and one of $R_2$, $R_3$ and $R_4$ is hydrogen and the other two together are $C_{1-2}$ alkylenedioxy, or the other two are the same or different and are selected from hydrogen, halogen, trifluoromethyl, $C_{1-6}$ alkyl, $C_{1-6}$ alkoxy, $C_{1-6}$ alkylthio, $C_{1-7}$acyl, $C_{1-7}$ acylamino, $C_{1-6}$alkylsulphonyl, $C_{1-6}$alkylsulphinyl hydroxy, nitro or amino, aminocarbonyl or aminosulphonyl optionally N-substituted by one or two $C_{1-6}$alkyl, $C_{3-8}$ cycloalkyl, phenyl or phen $C_{1-4}$alkyl groups or optionally N-disubstituted by $C_{4-5}$ polymethylene, or $R_1$ and $R_2$ together are $C_{1-2}$ alkylenedioxy, and $R_3$ and $R_4$ together are $C_{1-2}$ alkylenedioxy or $R_3$ and $R_4$ are the same or different and are selected from the previously defined class of substituents;
$R_5$ is hydrogen or as defined with $R_1$;
$R_6$ is hydrogen or $C_{1-6}$ alkyl; and
Ar is phenyl or thien-2-yl or thien-3-yl, optionally substituted by one or two groups, which are the same or different, selected from $C_{1-4}$ alkoxy, trifluoromethyl, halogen, carboxy, esterified carboxy or $C_{1-4}$ alkyl optionally substituted by hydroxy, $C_{1-4}$alkoxy, carboxy, esterified carboxy or in vivo hydrolysable $C_{1-4}$acyloxy, Ar being in the 3β configuration as defined in formula (VIII) hereinafter; and Ar may also have the 3α-configuration either when one of $R_2$, $R_3$ and $R_4$ is hydrogen and the other two are independently selected from optionally substituted amino or aminosulphonyl as defined, $C_{1-6}$ alkylsulphonyl or $C_{1-6}$ alkylsulphinyl; or $R_1$ and $R_2$ together are $C_{1-2}$ alkylenedioxy and $R_3$ and $R_4$ are independently selected from the same group of substituents.

Examples of $C_{1-6}$alkoxy, when $R_1$ and/or one or two of $R_2, R_3$ and $R_4$ include methoxy, ethoxy, n- and iso-propoxy and n-, iso-, sec-, and tert-butoxy.

Examples of $C_{1-6}$alkylthio, when $R_1$ and/or one or two of $R_2$, $R_3$ and $R_4$, include methylthio, ethylthio, n- and iso-propylthio and n-, iso-, sec- and tert-butylthio.

An example of $C_{1-2}$ alkylene, when $R_1$ and $R_5$ together, is methylene.

Examples of $C_{1-2}$alkylenedioxy, when two of $R_2$, $R_3$ and $R_4$ or when $R_1$ and $R_2$ and optionally $R_3$ and $R_4$, are methylenedioxy and ethylenedioxy.

Examples of halogen, when one or two of $R_2$, $R_3$ and $R_4$ include chloro and bromo.

Examples of $C_{1-6}$alkyl, when one or two of $R_2$, $R_3$ and $R_4$ or when one or both N-substituent(s) of amino, aminocarbonyl or aminosulphonyl, include methyl, ethyl, n- and iso-propyl and n-, iso-, sec- and tert-butyl.

A sub-class of $C_{1-7}$acyl, when one or two of $R_2$, $R_3$ and $R_4$, is $C_{1-4}$ alkanoyl, examples of which include acetyl, propionyl and n- and iso-butyryl.

A sub-class of $C_{1-7}$acylamino, when one or two of $R_2$, $R_3$ and $R_4$ is $C_{1-4}$alkanoylamino, examples of which include formylamino, acetylamino, propionylamino and n- and iso-butyrylamino.

Examples of $C_{1-6}$ alkylsulphonyl, when one or two of $R_2, R_3$ and $R_4$, include methylsulphonyl and ethylsulphonyl.

Examples of $C_{1-6}$alkylsulphinyl, when one or two of $R_2, R_3$ and $R_4$, included methylsulphinyl and ethylsulphinyl.

An example of $C_{3-8}$cycloalkyl, when an N-substituent, is cyclohexyl.

An example of phen $C_{1-4}$alkyl, when an N-substituent, is benzyl.

Examples of amino, aminocarbonyl and aminosulphonyl, when N-disubstituted by $C_{4-5}$polymethylene, are pyrrolidino, piperidino, pyrrolidinocarbonyl, piperidinocarbonyl, pyrrolidinosulphonyl and piperidinosulphonyl.

Preferably, $R_5$ is hydrogen.

Preferred compounds of formula (I) are those of formula (II); or a pharmaceutically acceptable salt, or N-oxide thereof; or a solvate of any of the foregoing:

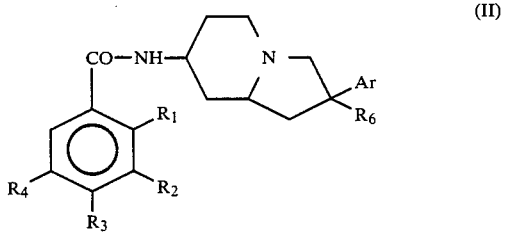

(II)

wherein Ar and $R_6$ are as defined hereinbefore and wherein $R_1$ is $C_{1-6}$ alkoxy, one of $R_2$, $R_3$ and $R_4$ is hydrogen and the other two are the same or different and are selected from the class of hydrogen, chloro, bromo, amino, $C_{1-6}$ alkylthio, trifluoromethyl, $C_{1-4}$ alkanoylamino, $C_{1-6}$ alkylsulphonyl, $C_{1-6}$alkylsulphinyl, $C_{1-6}$alkoxy, hydroxy or aminosulphonyl optionally N-substituted by one or two $C_{1-6}$alkyl groups, or $R_1$ and $R_2$ together are methylenedioxy or ethylenedioxy, and $R_3$ and $R_4$ are the same or different and are selected from the previously defined class of substituents.

Compounds falling within formula (II) are those in which $R_1$ is $C_{1-6}$alkoxy, one of $R_2$, $R_3$ and $R_4$ is hydrogen and the other two are the same or different and are selected from the class of hydrogen, $C_{1-6}$alkylsulphonyl, $C_{1-6}$alkylsulphinyl, $C_{1-6}$alkoxy, hydroxy or aminosulphonyl optionally N-substituted by one or two $C_{1-6}$alkyl groups, or $R_1$ and $R_2$ together are methylenedioxy or ethylenedioxy and $R_3$ and $R_4$ are the same or different and are selected from the previously defined class.

Preferred compounds falling within formula (II) include those wherein $R_1$ is methoxy, $R_2$ is hydrogen, or methoxy, $R_3$ is amino or hydrogen, and $R_4$ is chloro, hydrogen or aminosulphonyl, in which one of $R_2$, $R_3$ and $R_4$ is hydrogen.

Additionally, preferred compounds falling within formula (II) are those in which $R_1$ is methoxy, $R_2$ is hydrogen $R_3$ is amino optionally N-substituted by $C_{1-4}$alkanoyl, and $R_4$ is chloro.

$R_6$ may be hydrogen, methyl or ethyl, in particular hydrogen.

Examples of $C_{1-4}$alkoxy, when a phenyl or thienyl substituent, include methoxy and ethoxy.

Examples of halogen, when a phenyl or thienyl substituent, include bromo, chloro or fluoro.

When phenyl or thienyl is substituted by optionally substituted $C_{1-4}$alkyl, examples of $C_{1-4}$alkyl include methyl, ethyl and n-propyl; methyl however is most preferred. Examples of substituents of such alkyl groups include hydroxy, methoxy and ethoxy, carboxy, esterified carboxy, and in vivo hydrolysable acyloxy. The substitution preferably occurs on the terminal carbon atom of the alkyl group.

Examples of esterified carboxy groups include $C_{1-4}$alkoxycarbonyl, such as methoxy-, ethoxy-, n- and iso-propoxy-carbonyl, phenoxycarbonyl or benzyloxycarbonyl optionally substituted in the phenyl ring by one or two substituents selected from $C_{1-4}$alkyl, $C_{1-4}$ alkoxy, trifluoromethyl, halogen or nitro.

Examples of in vivo hydrolysable acyloxy groups include $C_{2-6}$alkanoyloxy, for example acetoxy, propionoxy, n- and iso-butyroxy, and 2,3-dimethylpropanoyloxy, benzyloxy or benzenesulphonyloxy either being optionally substituted in the phenyl ring by one or two substituents selected from $C_{1-4}$alkyl, $C_{1-4}$alkoxy, trifluoromethyl, halogen or nitro, or sulphonyloxy groups, for example $C_{1-6}$alkanesulphonyloxy group, such as methanesulphonyloxy.

Preferably, Ar is phenyl optionally substituted as hereinbefore defined. Particularly preferred are unsubstituted phenyl and monosubstituted phenyl, in particular ortho- or para-mono-substituted phenyl. Examples of substituents include methyl, fluoro, chloro, bromo. Ortho- and para-fluoro substituents are preferred. Para-fluoro is most preferred.

Within formula (II) is a sub-class of compounds of formula (III), or a pharmaceutically acceptable salt, or solvate of either of the foregoing:

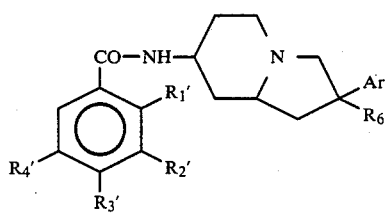
(III)

wherein $R_1'$ is $C_{1-6}$alkoxy and one of $R_2'$, $R_3'$ and $R_4'$ is hydrogen and the other two are the same or different and are each hydrogen halogen, hydroxy, $C_{1-6}$alkoxy, $C_{1-6}$alkylthio, trifluoromethyl, amino or $C_{1-4}$ alkanoylamino and $R_6$ and Ar are as defined hereinbefore.

Within formula (III) are a number of sub-classes, wherein $R_6$ and Ar are as hereinbefore defined, as indicated below; or hydrogen;

(a) $R_1'$ is methoxy, $R_2'$ is methoxy, $R_3'$ is hydrogen and $R_4'$ is methylthio
(b) $R_1'$ is methoxy, $R_2'$ and $R_3'$ are both hydrogen; and $R_4'$ is trifluoromethyl and in particular
(c) $R_1'$ is methoxy, $R_2'$ is hydrogen, $R_3'$ is amino or $C_{1-4}$alkanoylamino and $R_4'$ is chloro.

Within formula (II) is another sub-class of formula (IV), or a pharmaceutically acceptable salt or N-oxide thereof; or solvate of any of the foregoing:

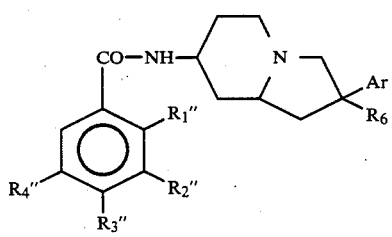
(IV)

wherein $R_1''$ is $C_{1-6}$alkoxy, one of $R_2''$, $R_3''$ and $R_4''$ is hydrogen and the other two are the same or different and are selected from the class of hydrogen, $C_{1-6}$alkylsulphonyl, $C_{1-6}$alkylsulphinyl or amino or aminosulphonyl optionally N-substituted by one or two $C_{1-6}$alkyl groups, or $R_1''$ and $R_2''$ together are methylenedioxy or ethylenedioxy and $R_3''$ and $R_4''$ are the same or different and are selected from the previously defined class of substituents, and $R_6$ and Ar are as defined hereinbefore in a sub-class (a) of compounds within formula (IV), neither of the other two of $R_2'', R_3''$ and $R_4''$ is hydrogen, and Ar may also be in the α-configuration.

Within the formulae (III), and sub-classes (a) to (c) thereof, and (IV) are further sub-classes of compounds, wherein Ar is phenyl optionally substituted as hereinbefore defined.

Within each of these sub-classes, there are compounds of formulae (III), and sub-classes (a) to (c) thereof and (IV) wherein Ar is unsubstituted phenyl.

Within each of these sub-classes, there are compounds of formulae (III), and sub-classes (a) to (c) thereof, and (IV), wherein Ar is phenyl substituted by one or two groups, which are the same or different, selected from $C_{1-4}$alkoxy, trifluoromethyl, halogen, carboxy, esterified carboxy, or $C_{1-4}$alkyl optionally substituted by hydroxy, $C_{1-4}$alkoxy, carboxy, esterified carboxy or in vivo hydrolysable acyloxy.

Particularly preferred compounds of each of formulae (III) and (IV) are those wherein Ar is phenyl optionally substituted in the phenyl ring by one or two groups selected from $C_{1-4}$alkoxy, trifluoromethyl, halogen and $C_{1-4}$alkyl.

It is especially preferred that the phenyl ring is monosubstituted, that the substitution is in the para-position and/or that the substituent is chloro, fluoro or methyl.

The compounds of formulae (I) to (IV) have three asymmetric centres and thus are capable of existing in a number of stereoisomeric forms. The present invention extends to all of these forms individually and to mixtures of such stereoisomers including racemates.

It is preferred that in formulae (I) to (IV) the moiety of formula (V):

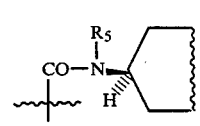
(V)

wherein $R_5$ is as hereinbefore defined, is in the β-configuration shown.

It is preferred that in formulae (I) to (IV) the moiety of formula (VI):

(VI)

is in the α-configuration shown.

In formulae (I) to (IV) the moiety of formula (VII):

(VII)

wherein $R_6$ is as hereinbefore defined is in the β-configuration shown except in sub-formula(IV) (a) when it may also be in the α-configuration.

The most preferred configuration for the compounds of formula (I) includes each of the configurations of formulae (V) to (VII), as shown in formula (VIII):

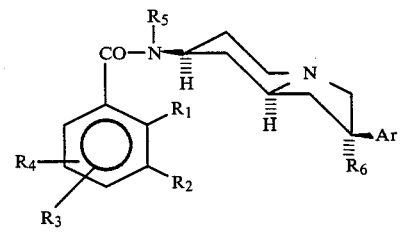
(VIII)

and its enantiomer, wherein $R_1$ to $R_6$ and Ar are as hereinbefore defined.

The most preferred configuration for the compounds of the formula (IV) (a) for anti-hypertensive and anti-arrhythmic activity (discussed further hereinafter) is as shown in formula (IX); and its enantiomer:

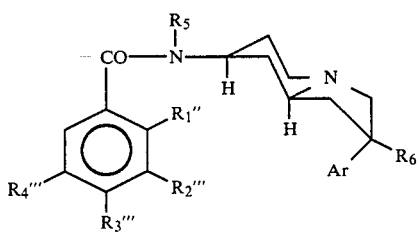

wherein R$_2'''$, R$_3'''$ and R$_4'''$ are R$_2''$, R$_3''$ and R$_4''$ as defined in formula (IV) (a).

The pharmaceutically acceptable salts of the compounds of this invention include acid addition salts with conventional acids such as hydrochloric, hydrobromic, phophoric, sulphuric, citric, tartaric, lactic and acetic acid, and quaternary salts with alkyl, phenalkyl and cycloalkyl halides. Suitable examples of such quaternising agents include methyl, ethyl, n- and iso-propyl, benzyl and phenethyl chlorides, bromides and iodides. Solvent adducts include hydrates and adducts with organic solvents such as chloroform.

The present invention also provides a process for preparing a compound of formula (I), or a pharmaceutically acceptable salt or N-oxide thereof or a solvate of any of the foregoing, which comprises reacting a compound of formula (X):

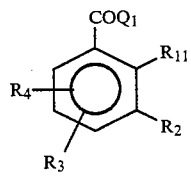

with a compound of formula (XI)

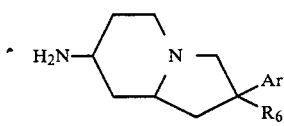

wherein R$_2$ to R$_4$, R$_6$ and Ar are as defined hereinbefore: R$_{11}$ is R$_1$ as defined, or $(CH_2)_m$ CR$_7$R$_8$Q$_2$ where Q$_1$ and Q$_2$ are the same or different and are leaving groups or together are O, R$_7$ and R$_8$ are both hydrogen or, together with the carbon atom to which they are attached, are a carbonyl group, m is 0 or 1; and in the case where R$_7$ and R$_8$, together with the carbon atom to which they are attached, are a carbonyl group, reducing the carbonyl group in the thus formed compound to a methylene group; optionally converting R$_2$, R$_3$,R$_4$ or Ar in the thus formed compound to another R$_2$, R$_3$, R$_4$ or Ar within formula (I); and optionally forming a pharmaceutically acceptable salt or N-oxide of the thus formed compound.

The leaving groups Q$_1$ and Q$_2$ are groups that are readily displaceable by a nucleophile. Examples of such groups are hydroxy, halogen such as chloro and bromo, and for Q$_1$ and Q$_2$, when R$_7$ and R$_8$ together with the carbon atom to which they are attached are a carbonyl group, acyloxy such as C$_{1-4}$ alkanoyloxy, C$_{1-4}$ alkoxycarbonyloxy and activated hydrocarbyloxy such as pentachlorophenoxy.

If a leaving group is hydroxy, then the reaction is preferably carried out in an inert non-hydroxylic solvent, such as benzene, toluene or diethyl ether in the presence of a dehydrating catalyst, such as a carbodiimide, for example dicyclohexylcarbodiimide. The reaction may be carried out at a non-extreme temperature such as $-10°$ to $100°$ C., for example 0° to 80° C.

If a leaving group is a halide, then the reaction is preferably carried out at a non-extreme temperature in an inert non-hydroxylic solvent, such as benzene, toluene or diethyl ether. It is also preferably carried out in the presence of an acid acceptor, such as an organic base, in particular a tertiary amine, such as triethylamine, trimethylamine, pyridine or picoline, some of which can also function as the solvent. Alternatively, the acid acceptor can be inorganic, such as calcium carbonate, sodium carbonate or potassium carbonate.

If a leaving group is acyloxy, then the reaction is preferably carried out in substantially the same manner as if the leaving group were hydroxy. Suitable examples of acyloxy leaving groups include C$_{1-4}$ alkanoyloxy, mesyloxy, tosyloxy and triflate.

If a leaving group is C$_{1-4}$ alkoxycarbonyloxy, then the reaction is preferably carried out in an inert solvent, such as methylene chloride, at a non-extreme temperature in the presence of an acid acceptor, such as triethylamine.

If a leaving group is activated hydrocarbyloxy then the reaction is preferably carried out in an inert polar solvent, such as dimethylformamide. It is also preferred that the activated hydrocarbyloxy group is a pentachlorophenyl ester and that the reaction is carried out at ambient temperature.

Preferably Q$_1$ is halogen, such as chloro.

When R$_7$ and R$_8$ are both hydrogen, Q$_2$ preferably is halogen, mesyloxy, tosyloxy, triflate or hydroxy. Q$_2$ may also be C$_{1-4}$alkanoyloxy or activated hydrocarbyloxy. Conveniently, Q$_1$ and Q$_2$ are the same, in particular the same halogen.

When R$_7$ and R$_8$, together with the carbon atom to which they are attached, are a carbonyl group, Q$_2$ is preferably an activated hydrocarbyloxy group. Alternatively, Q$_1$ and Q$_2$ together are 0, thus forming a derivative of phthalic anhydride (when m=0) or of homophthalic anhydride (when m=1).

Where in formula (X), R$_7$ and R$_8$, together with the carbon atom to which they are attached, are a carbonyl group, the reduction of the carbonyl group in the thus formed compound is preferably carried out, with or without isolation of the compound, by reduction with tin/hydrochloric acid at a non-extreme temperature.

The compounds of formula (X) are either known compounds or can be prepared analogously to the preparation of structurally similar known compounds, by known methods; for example the compound, wherein m is 0 and Q$_2$ is bromo can be prepared by reacting a compound of formula (XII):

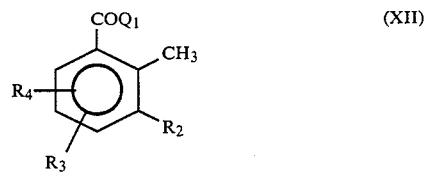

wherein R$_2$ to R$_4$ and Q$_1$ are as defined hereinbefore, with a brominating agent, such as N-bromosuccinimide.

The corresponding chloromethyl compound can be obtained similarly and this can then be base hydrolysed or acylated to give the corresponding compound of formula (X), wherein $R_7$ and $R_8$ are both hydrogen and $Q_2$ is hydroxy or acyloxy respectively.

Alternatively, those compounds of formula (X), wherein m is 0 or 1, and $Q_1$ and $Q_2$ together are O, can be prepared by known methods from phthalic or homophthalic acids respectively, for example by reflux with acetic anhydride.

Compounds of formula (XI) can be prepared by reduction of the oxime of formula (XIII):

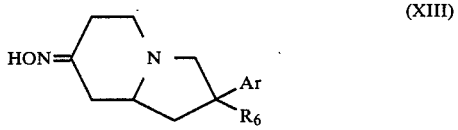

wherein Ar and $R_6$ are as defined hereinbefore.

The reducing agent may be sodium and amyl alcohol, lithium aluminium hydride or a catalytic reducing agent, such as hydrogen and nickel.

The oxime of formula (XIII) can be prepared by reacting the compound of formula (XIV):

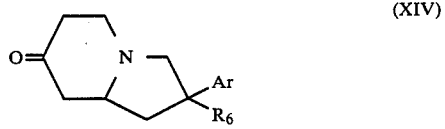

wherein $R_6$ and Ar are as defined hereinbefore, with hydroxylamine.

Compounds of the formula (XI), (XIII) and (XIV) are believed to be novel compounds, and accordingly form an aspect of the present invention.

The compound of formula (XIV) can be prepared by reacting a compound of formula (XV):

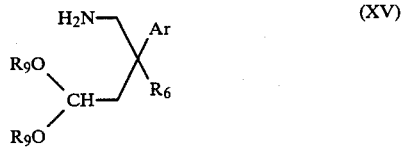

wherein Ar and $R_6$ are as defined hereinbefore and $R_9$ is $C_{1-4}$alkyl or both $R_9$'s together are $C_{1-4}$alkylene, with methyl vinyl ketone, to form a compound of formula:

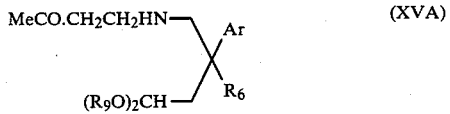

which is then bicyclised to the compound of formula (XIV).

The latter reaction is conveniently carried out using an acid addition salt of the compound of formula (XVA) in a polar hydroxylic solvent such as water at a moderately elevated temperature such as 80°–100° C.

The preparative processes for the intermediates of formulae (X), (XIII) and (XIV) also form an aspect of the present invention.

Preferred examples of $R_9$ are methyl and ethyl.

The reaction is conveniently carried out in an inert solvent, such as ether, at room temperature.

The compound of formula (XV) can be prepared by reduction of a compound of formula (XVI):

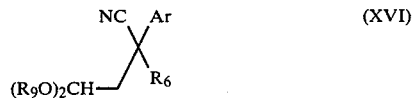

wherein $R_6$, $R_9$ and Ar are as hereinbefore defined.

The reduction is preferably carried out under nitrogen with lithium aluminium hydride in an inert solvent in the presence of aluminium chloride or concentrated sulphuric acid.

The compound of formula (XVI) can be prepared by the process described by Poulain, G, in *Bull. Soc. Chim. Fr.*, 1964, 913.

Compounds of the formula (XV), (XVA) and those of (XVI) and their precursors not specifically disclosed by *Bull. Soc. Chim. Fr.*, 1964,913 are also believed to be novel, and accordingly form an aspect of the present invention. The preparative processes for all these compounds also form an aspect of the present invention.

Compounds of formula (I), wherein $R_2$, $R_3$ or $R_4$ is convertible to another $R_2$, $R_3$ or $R_4$ within formula (I), are useful intermediates. A number of such conversions is possible not only for the end compounds of formula (I), but also for their intermediates as follows:

(a) an hydrogen substituent is convertible to a nitro substituent by nitration;

(b) a nitro substituent is convertible to an amino substituent by reduction;

(c) a $C_{1-4}$acylamino substituent is convertible to an amino substituent by deacylation;

(d) an amino substituent is convertible to a $C_{1-4}$acylamino substituent by acylation.

(e) a hydrogen substituent is convertible to a halogen substituent by halogenation; and (f) a $C_{1-6}$alkylthio or $C_{1-6}$alkylsulphinyl substituent is convertible to a $C_{1-6}$alkylsulphinyl or a $C_{1-6}$alkylsulphonyl substituent respectively by oxidation Conversions (a) to (f), are only exemplary and are not exhaustive of the possibilities.

In regard to (a), nitration is carried out in accordance with known procedures.

In regard to (b), the reduction is carried out with a reagent suitable for reducing nitroanisole to aminoanisole.

In regard to (c), deacylation is carried out by treatment with a base, such as an alkali metal hydroxide.

In regard to (d), the acylation is carried out with an acylating agent, such as the corresponding acid or acid chloride. Formylation is carried out with the free acid.

In regard to (e), halogenation is carried out with conventional halogenating agents.

In regard to (f), oxidation is carried out at below ambient temperatures in a non-aqueous solvent, such as a chlorinated hydrocarbon, in the presence of an organic peracid, such as 3-chloroperbenzoic acid, or in water in the presence of a soluble strong inorganic oxidant, such as an alkali metal permanganate or in aqueous hydrogen peroxide.

Before carrying out any of these conversions, the effect, if any, on other substituents should be considered and such reagents as are appropriate should be selected together with the adoption of such precautionary measures as are necessary. For example, the oxidation (f) may also product the N-oxide of the bicyclic ring system and may also oxidise an hydroxyalkyl substituent, of an Ar phenyl or thienyl group, if present. Consequently, if such additional oxidation is to be avoided, then the reaction is desirably carried out on the intermediate of formula (X).

Compounds of formula (I), wherein Ar is phenyl or thienyl optionally substituted as previously defined are interconvertible. A number of such interconversions are possible not only for the end compounds of formula (I), but also for their intermediates as follows:

(i) a carboxy $C_{1-4}$alkyl substituent is convertible to an esterified carboxy $C_{1-4}$alkyl substituent by esterification;

(ii) an esterified carboxy $C_{1-4}$alkyl substituent is convertible to a carboxy $C_{1-4}$alkyl substituent by deesterification;

(iii) $C_{1-4}$alkoxy $C_{1-4}$alkyl substituent or an in vivo hydrolysable $C_{1-4}$acyloxy $C_{1-4}$alkyl substituent is convertible to an hydroxy $C_{1-4}$alkyl substituent;

(iv) an optionally esterified carboxy or carboxy $C_{1-3}$alkyl substituent is convertible to an hydroxymethyl or hydroxy $C_{2-4}$alkyl substituent by reduction; and (v) a hydroxy $C_{1-4}$alkyl is convertible to $C_{1-4}$alkoxy $C_{1-4}$alkyl by O-alkylation or to in vivo hydrolysable $C_{1-4}$acyloxy $C_{1-4}$alkyl by O-acylation.

Conversions (i) to (iv) are only exemplary and are not exhaustive of the possibilities.

In regard to (i) and (ii), the esterification and deesterification reactions are carried out in conventional manner.

In regard to (iii), a $C_{1-4}$alkoxy $C_{1-4}$alkyl substituent is convertible to an hydroxy $C_{1-4}$alkyl substituent by conventional methods, such as warming with aqueous hydrobromic acid or by treatment with pyridine hydrochloride, boron tribromide boron triodide or iodotrimethylsilane.

An in vivo hydrolysable $C_{2-4}$acyloxy $C_{1-4}$alkyl substituent is convertible to an hydroxy $C_{1-4}$alkyl substituent by acid or base hydrolysis.

In regard to (iv), the reduction is carried out with a selective metal complex hydride, for example lithium aluminium hydride, under conventional conditions.

In regard to (v), O-alkylation is carried out under conventional conditions in an inert solvent at a non-extreme temperature such as ambient temperature or slightly above or at reflux temperature. The $C_{1-4}$alkylating agent has a leaving group that is readily displaceable by a nucleophile. Examples of leaving groups include halide, such as chloride, bromide or iodide, or labile acyloxy groups, such as mesyl and tosyl.

O-acylation is carried out under conventional conditions with an acylating agent which has an acyl group capable of forming an in vivo hydrolysable acyloxy group and a leaving group, such as halide, for example chloride and bromide, and hydroxy. When halide is the leaving group, the reaction is generally carried out in the presence of a base. When hydroxy is the leaving group, the reaction is generally carried out in the presence of a dehydrating agent, such as dicyclohexylcarbodiimide, in an inert solvent at non-extreme temperature, such as ambient temperature or slightly above, or reflux temperature.

Before carrying out any of these conversions, the effect, if any, on other substituents should be considered and such reagents as are appropriate should be selected together with the adoption of such precautionary measures as are necessary. For example, O-alkylation and O-acylation may also produce N-alkylated and N-acylated products respectively unless the nitrogen atom(s) is (are) previously protected. This may be conveniently achieved by carrying out the alkylation or acylation reaction in a strong acid, such as trifluoroacetic acid, which protonates, and thereby protects, the nitrogen atom(s).

As mentioned hereinbefore, the compounds of formula (I) exist in a number of stereoisomeric forms. A mixture of such forms can be obtained from a non-stereospecific mixture of intermediates and then the desired isomer separated conventionally from the product mixture by, for example, chromatography. Alternatively, the isomers can be obtained from specific intermediate isomers.

By way of example the preferred $3\alpha$- or $3\beta$-isomer and the preferred $5\alpha$-isomer in formulae (IX), (VIII) and (VI) respectively, can be prepared from the corresponding isomers of the intermediate of formula (XI) prepared and separated by the process described in *Bull. Soc. Chim. Fr*, 1964, 913, or prepared by that process from the specific corresponding enantiomers of compounds of the formula (XV).

The preferred $7\beta$-isomer, as shown in formula (V), can be prepared by carrying out the reduction of the oxime of formula (XIII) with sodium and amyl alcohol.

The less preferred $7\alpha$-isomer can be prepared by carrying out the reduction of the oxime of formula (XIII) with hydrogen and a nickel catalyst in ammonium acetate.

A mixture of $7\alpha$- and $7\beta$-isomers can be prepared by carrying out the reduction of the oxime of formula (XIII) with lithium aluminium hydride.

Pharmaceutically acceptable salts, and N-oxides of the compounds of this invention may be formed conventionally. The salts may be formed for example by reaction of the base compound of formula (I) with a pharmaceutically acceptable organic or inorganic acid.

Quaternary salts may be prepared by reaction of a compound of the present invention with the appropriate alkyl, aryl or aralkyl chloride, bromide or iodide. This reaction may be carried out in a solvent, such as acetone, methanol, ethanol, dimethylformamide at ambient or elevated temperature with or without pressure.

N-oxides of the nitrogen atom of the bicyclic ring system are produced by reaction of a compound of formula (I) with an organic peracid, such as m-chloroperbenzoic acid in, for example, a chlorinated hydrocarbon solvent at below ambient temperature.

The compounds of the present invention are dopamine antagonists and may generally be used in the treatment of emesis. Depending on their balance between peripheral and central action on the nervous system, they may also be used in the treatment of disorders relating to impaired gastro-intestinal motility, such as retarded gastric emptying, dyspepsia, flatulence, oesophagal reflux and peptic ulcer, and/or in the treatment of disorders of the central nervous system, such as psychosis.

Those compounds of the present invention, which are of particular interest for their CNS activity, are those of formula (III) and sub-classes (a) to (c) thereof, in particular sub-class (c) thereof.

Those compounds of the present invention which are of interest for their beneficial effect on gastric motility are the quaternary salts and N-oxides of such compounds, in particular the quaternary salts of the compounds of formula (IV).

The invention also provides a pharmaceutical composition comprising a compound of the present invention, or a pharmaceutically acceptable salt or N-oxide thereof or a solvate of any of the foregoing and a pharmaceutically acceptable carrier.

Such compositions are prepared by admixture and are suitably adapted for oral or parenteral administration, and as such may be in the form of tablets, capsules, oral liquid preparations, powders, granules, lozenges, reconstitutable powders, injectable and infusable solutions or suspensions or suppositories. Orally administerable compositions are preferred.

Tablets and capsules for oral administration are usually presented in a unit dose, and contain conventional excipients such as binding agents, fillers, tabletting agents lubricants, disintegrants, and wetting agents. The tablets may be coated according to well known methods in the art. Oral liquid preparations are usually in the form of aqueous or oily suspensions, solutions, emulsions, syrups, or elixirs, or are presented as a dry product for reconstitution with water or other suitable vehicle before use. Such liquid preparations may contain conventional additives such as suspending agents, emulsifying agents, non-aqueous vehicles (which may include edible oils), preservatives, and flavouring or colouring agents.

For parenteral administration, fluid unit dose forms are prepared containing a compound of the present invention and a sterile vehicle. The compound, depending on the vehicle and the concentration, can be either suspended or dissolved. Parenteral solutions are normally prepared by dissolving the compound in the vehicle and filter sterilizing before filling into a suitable vial or ampoule and sealing. Advantageously, adjuvants such as a local anaesthetic, preservatives and buffering agents are also dissolved in the vehicle.

Parenteral suspensions are prepared in substantially the same manner except that the compound is suspended in the vehicle instead of being dissolved and sterilized by exposure to ethylene oxide before suspending in the sterile vehicle. Advantageously, a surfactant or wetting agent is included in the composition to facilitate uniform distribution of the compound of the invention.

The invention further provides a method of treatment or prophylaxis of emesis or disorders of the central nervous system in mammals, such as humans, which comprises the administration of an effective amount of a compound of the present invention, or a pharmaceutically acceptable acid addition salt thereof, or a solvate of either of the foregoing.

The invention further provides a method of treatment or prophylaxis of disorders related to impaired gastro-intestinal motility in mammals, such as humans, which comprises the administration of an effective amount of a compound of the present invention, or a pharmaceutically acceptable salt thereof, or N-oxide thereof, or a solvate of any of the foregoing.

An amount effective to treat the disorders hereinbefore described depends on the relative efficacies of the compounds of the invention, the nature and severity of the disorder being treated and the weight of the mammal. However, a unit dose will normally contain 0.1 to 20 mg for example 0.5 to 10 mg, of the compound of the invention. Unit doses will normally be administered more than once a day, for example 2, 3, 4, 5 or 6 times a day such that the total daily dose is normally in the range 0.01 to 10 mg/kg per day.

The invention provides a compound of the present invention or a pharmaceutically acceptable acid addition salt thereof, or a solvate of either of the foregoing for the treatment or prophylaxis of emesis or disorders related to impaired gastro-intestinal motility or of the central nervous system.

The invention also provides a quaternary salt or N-oxide of a compound of the present invention or a solvate thereof for the treatment or prophylaxis of disorders related to impaired gastro-intestinal motility.

The compounds of the present invention also have the ability to potentiate the effect of conventional analgesics in migraine treatment when administered concurrently with the analgesic.

Accordingly, the present invention also provides a pharmaceutical composition comprising a compound of the present invention or a pharmaceutically acceptable salt or N-oxide thereof or a solvate of any of the foregoing, and an analgesic.

The compound of the present invention and the analgesic such as aspirin or paracetamol, are present in the composition in amounts generally similar to their usual effective dose.

The composition can be a combination product, for example a tablet or capsule containing both a compound of the invention and an analgesic for oral administration, or a twin pack comprising the two active ingredients made up for separate administration.

The invention accordingly provides a method of treatment of migraine in mammals including humans comprising the administration of an effective amount of a compound of the invention or a pharmaceutically acceptable salt or N-oxide thereof or a solvate of any of the foregoing and an analgesic.

Compounds of formula (IV) (a) also have antihypertensive and antiarrhythmic activity.

The present invention thus provides a compound of the formula (IV) (a) or a pharmaceutically acceptable salt or N-oxide thereof, or a solvate of any of the foregoing for use in the treatment or prophylaxis of hypertension or cardiac arrhythmia.

The invention also provides a method of treatment or prophylaxis of cardiac arrhythmia in mammals including humans, comprising the administration to a sufferer of a therapeutically effective amount of a compound of the formula (IV)(a) a pharmaceutically acceptable salt thereof, or an N-oxide thereof, or a solvate of any of the foregoing.

The present invention yet further provides a method of treatment or prophylaxis of hypertension in mammals including humans, which comprises administering to the suffering mammal an anti-hypertensive effective amount of a compound of the formula (IV) (a) a pharmaceutically acceptable salt thereof, or an N-oxide thereof, or a solvate of any of the foregoing.

The effective amount will be similar to those indicated hereinbefore for the dopamine-related utilities.

The following examples illustrate the preparation of compounds of the invention and the following descriptions illustrate the preparation of intermediates.

DESCRIPTION 1

(a)

(±) 4,4-Diethoxy-2-Phenylbutylamine (D.1a)
Intermediate for Compounds 1a and 2a.

D.1a

To a stirred suspension of lithium aluminium hydride (1.9 g) in dry ether (100 mls) under nitrogen, was added a solution of aluminium chloride (2.3 g) in ether (50 ml) at 0° C. After 30 minutes a solution of (±) 3,3-diethoxy-1-phenylpropionitrile (12 g) (G. Poulain; *Bull. Soc. Chim.,* (Fr) 1964, 913) in ether (50 ml) was added and the reaction mixture stirred to room temperature for 4 hours. Normal work-up procedure (Fieser method) gave the (±) 4,4-diethoxy-2-phenyl butylamine (D.1a) bp 120°/0.1 mm (11 g, 90%).

Following the procedures outlined above, the following amines were prepared:

(b)

(±) 4,4-Diethoxy-2-p-fluorophenylbutylamine (D.1b)
(bp 140°/1 mm 70%).
intermediate for compounds 1b and 2b.

(c)

(±) 4,4-Diethoxy-2-methyl-2-phenylbutylamine (D.1c)
(bp 120°/0.1 mm 95%).
intermediate for compounds 1c and 2c.

(d)

(±) 4,4-Diethoxy-2-o-fluorophenylbutylamine (D.1d)
(bp 125°/0.1 mm 75%).
intermediate for compound 2d.

DESCRIPTION 2

(±) 3β-Phenyl-1-aza-5αH-bicyclo[4,3,0]nonan-7-one (D.2a)

Intermediate for compounds 1a and 2a.

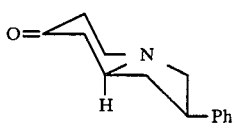
D.2a

Methyl vinyl ketone (4 ml) was added to a solution of (±) 4,4-diethoxy-2-phenylbutylamine (D.1a) (9.6 g) in ether (10 ml) and the solution stirred at room temperature for 30 minutes. The amine was extracted into 2.5N hydrochloric acid (50 ml) and the aqueous extract heated on a steam bath for 2 hours. On cooling, the solution was basified and extracted with methylene chloride. Purification of the concentrated extract (silica/ether) afforded the (±) 3β-phenyl-1-aza-5αH-bicyclo[4,3,0]nonan-7-one (D.2a) (1.2 g, 14%).

Following the procedures outlined above, the following ketones were prepared:

(b)

(±) 3β-p-Fluorophenyl-1-aza-5αH-bicyclo[4,3,0]nonan-7-one (D.2b) (19%)
intermediate for compounds 1b and 2b.
M.S. Found 233.1222, Theory 233.1216.

(c)

(±) 3-Methyl-3-phenyl-1-aza-5αH-bicyclo[4,3,0]nonan-7-one (D.2c) (isomer1) (80%)
intermediate for compounds 1c and 2c.

(d)

(±) 3β-o-Fluorophenyl-1-aza-5αH-bicyclo[4,3,0]nonan-7-one (D.2d) (88%)
(mixture of 3α and 3β-o-fluorophenyl)
intermediate for compound 2d.

DESCRIPTION 3

(±)
7β-Amino-3β-phenyl-1-aza-5αH-bicyclo[4,3,0]nonan (D.3a)

intermediate for compounds 1a and 2a.

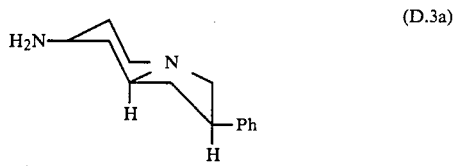
(D.3a)

D.2a (1.8 g) (prepared as in Description 2a) was oximated by the standard procedure (hydroxylamine hydrochloride/pyridine/ethanol) to give the crude oxime (1.7 g 50%).

The oxime (1.7 g) was dissolved in amyl alcohol (30 mls) and heated to reflux when sodium (2.0 g) was added over 10 minutes. When all the sodium had dissolved, the reaction was cooled and treated with 5N hydrochloric acid (50 ml). The aqueous layer was extracted with ether (2× 100 ml), saturated with potassium carbonate and re-extracted with methylene chloride. Concentration of the methylene chloride extract afforded the crude (±) 7β-amino-3β-phenyl-1-aza-5αH-bicyclo[4,3,0]nonane (D.3a) (1.6 g, 100%).

Following the procedures outlined above, the following amines were prepared:

(a)

(±) 7β-Amino-3β-p-fluorophenyl-1-aza-5αH[4,3,0]nonan (D.3b) (90%)
intermediate for compounds 1b and 2b.

(c)

(±) 7β-Amino-3-methyl-3-phenyl-1-aza-5αH-bicyclo[4,3,0]nonan (D.3c)
(bp 145°/0.5 mm, 80%).
intermediate for compounds 1c and 2c.

(d)

(±) 7β-Amino-3β-o-fluorophenyl-1-aza-5αH-bicyclo[4,3,0]nonan (D.3d)
(bp 120°/0.5 mm 35%).
intermediate for compounds 2d (mixture of 3α and 3β).

EXAMPLE 1a (±)
4-Acetamido-5-chloro-2-methoxy-N-[7′β-(3′β-phenyl-1′-aza-5′αH-bicyclo[4,3,0]nonyl)]benzamide (1a)

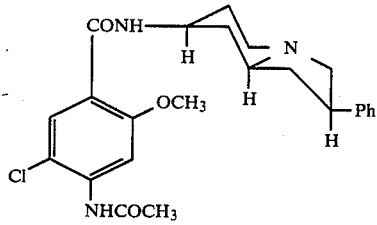

(1a)

To a solution of 4-acetamido-5-chloro-2-methoxybenzoic acid (2.0 g) in methylene chloride (200 mls) was added oxalyl chloride (0.75 ml) and 5 drops of dimethylformamide. The solution was stirred until the evolution of gas had ceased (ca. 1 hour). Triethylamine (3 mls) in methylene chloride (10 ml) and (±) 7β-amino-3β-phenyl-1-aza-5αH-bicyclo[4,3,0]nonane (D.1a) (1.6 g) in methylene chloride (10 ml) were added and the solution stirred at room temperature for 2 hours. On treatment with 2.5N sodium hydroxide (10 ml), the organic layer was separated, dried (K₂CO₃) and concentrated to give the crude product.

Purification by column chromatography (silica/ethyl acetate) afforded the (±) 4-acetamido-5-chloro-2-methoxy-N-[7′β-(3′β-phenyl-1′-aza-5αH-bicyclo[4,3,0]nonyl)]benzamide (1a) as an oil (2.3, 70%).
m.s. Found 441.1832 (Theory 441.1819).

Following the procedures outlined above, the following acetamides were prepared.

(1b)

(±) 4-Acetamido-5-chloro-2-methoxy-N-[7′β-3′β-p-fluorophenyl-1′-aza 5′α-H-bicyclo[4,3,0]nonyl)]benzamide (1b) (60%)
m.s. Found 459.1706 (Theory 459.1722).

(1c)

(±) 4-Acetamido-5-chloro-2-methoxy-N-[7′β-(3′-methyl-3′-phenyl-1′-aza-5′αH-bicyclo[4,3,0]nonyl)]benzamide (1c) (55%) (less polar isomer)
m.s. Found 455.1962 (Theory 455.1975).

EXAMPLE 2a (±)
4-Amino-5-chloro-2-methoxy-N-[7′β-(3′β-phenyl-1′-aza-5′αH-bicyclo[4,3,0]nonyl)]benzamide (2a)

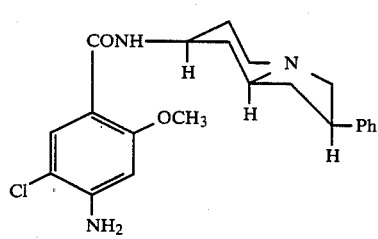

(2a)

(1a) (2.3 g) (Prepared as in Example 1a) was heated under reflux in ethanol (50 ml) and aqueous sodium hydroxide (2.5N, 5 ml) for 2 hours. On cooling, the ethanol was removed and the residue extracted with methylene chloride. Concentration of the organic extracts gave the (±) 4-amino-5-chloro-2-methoxy-N-[7′β-(3′β-phenyl-1′-aza-5′αH-bicyclo-[4,3,0]nonyl)]benzamide (2a), which was crystallized from ethyl acetate/petrol. (1.5 g, 7.5%) mp=167°–70°. M.S. Found 399.1704 (Theory 399.1713).

n.m.r. (δ,CDCl₃):
8.09 (s, 1H, aryl-6H)
7.5–7.7 (br.d., 1H, CONH)
7.5–7.0 (m. 5H, aryl H)
6.29 (s, 1H, aryl 3H)
4.7–3.8 (m, 6H, NH₂, 7′α-H including 3.85,s,3H, OCH₃)
3.5–1.0 (m, 12H, remaining protons)

Following the procedures outlined above, the following benzamides were prepared:

(2b)

(±) 4-Amino-5-chloro-2-methoxy-N-[7′β-(3′β-p-fluorophenyl-1′-aza-5′αH-bicyclo[4,3,0]nonyl)]benzamide (2b) (80%)
m.s. Found 417.1620 (Theory 417.1616).
Converted into its nonohydrochloride m.p. 249°–52°.

(2c)

(±) 4-Amino-5-chloro-2-methoxy-N-[7′β-[3′-methyl-3′-phenyl-1′-aza-5′αH-bicyclo[4,3,0]nonyl)]benzamide (2c) (less polar isomer) (70%)
m.s. Found 413.1865 (Theory 413.1867).
Converted into its monohydrochloride mp 238°–9°.
This isomer is thought to be the 3′α-methyl-3′β-phenyl isomer.

EXAMPLE 2d (±)
4-Amino-5-chloro-2-methoxy-N-(7′β-[3′-o-fluorophenyl-1′-aza-5′αH-bicyclo[4,3,0]nonyl)]benzamide (2d)

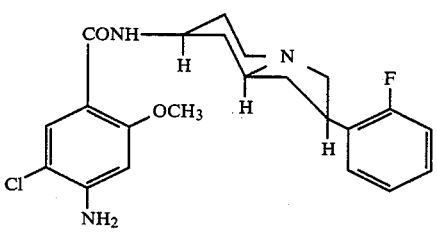

To a stirred suspension of 4-amino-5-chloro-2-methoxybenzoic acid (1.9 g) in methylene chloride (100 ml) and triethylamine (1.3 ml) was added ethyl chloroformate (0.92 ml) maintaining the temperature at ca. 25° with cooling. After stirring at room temperature for 30 minutes, the 7β-amino-3α,β-o-fluorophenyl-1-aza-5αH-bicyclo[4,3,0]nonan (D.3d) (2.0 g) in methylene chloride (10 ml) was added and the whole stirred at room temperature for 4 hours. Work up as previously described in Example 1a gave an oil, which on column chromatography (silica/ethyl acetate) gave the less polar isomer, (±) 4-amino-5-chloro-2-methoxy-N-[7′β-3′-o-fluorophenyl-1′-aza-5′αH-bicyclo[4,3,0]nonyl)-]benzamide (2d) (1.1 g, 30%) mp 98°–9°.

This isomer is thought to be the 3′β isomer.

Following the procedures outlined above, the following benzamides were prepared:

2(e)

(±) 4-Amino-5-methylsulphonyl-2-methoxy-N-[7'β-(3'β-phenyl-1'-aza-5'αH-bicyclo[4,3,0]nonyl)]benzamide (2e)

m.s, Found 443.1856 (Theory 443.1878).
Converted into its monohydrochloride mp 193°-4°.

2(f)

(±) 4-Amino-5-methylsulphonyl-2-methoxy-N-[7'β-(3'β-p-fluorophenyl-1'-aza-5'αH-bicyclo[4,3,0]nonyl)]benzamide (2f)

m.s. Found 461.1820 (Theory 461.1784).
converted into its monohydrochloride mp 189°-90°.

2(g)

(±) 4-Amino-5-methylsulphonyl-2-methoxy-N-[7'β-(3'α-phenyl-1'-aza-5'αH-bicyclo[4,3,0]nonyl)]benzamide (2g) isolated from the reaction mixture of 2(e).
m.p. 226°-9° C. as hemihydrate.

2(h)

(±) 4-Amino-5-methylsulphonyl-2-methoxy-N-[7'β-(3α-p-fluorophenyl-1'-aza-5'αH-bicyclo[4,3,0]nonyl)]benzamide 2(h) isolated from the reaction mixture of 2(f).

2(i)

(±) 5-trifluoromethyl-2-methoxy-N-(7'β-p-fluorophenyl-1'-aza-5'αH-bicyclo[4,3,0]nonyl)]benzamide (2i)

2(j)

(±) 2,3-dimethoxy-5-methylthio-N-[7'β-(3'β-p-fluorophenyl-1'-aza-5'αH-bicyclo[4,3,0]nonyl)]benzamide 2(j)

2(k)

(±) 4-Amino-5-chloro-2-methoxy-N-[7'β-(3'β-p-methylphenyl-1'-aza-5'αH-bicyclo[4,3,0]nonyl)]benzamide 2(k)

2(l)

(±) 4-Amino-5-chloro-2-methoxy-N-[7'β-(3'β-thienyl-1'-aza-5'αH-bicyclo[4,3,0]nonyl)]benzamide 2(l)

2(m)

(±) 2,3-dimethoxy-N-{7'β-(3β-p-fluorophenyl-1'-aza-5'αH-bicyclo{4,3,0}nonyl)}benzamide 2(m)

PHARMACOLOGICAL DATA

The results in the following table are an illustration of the anti-psychotic activity of the present compounds as shown by Inhibition of Apormorphine Induced Climbing in the Mouse, a standard test.

Inhibition of apomorphine induced climbing in the mouse

The test is based on that described by Protais, P., Constantin, J. and Schwartz J. C. (1976), Psychopharmacology, 50, 1–6.

When mice are given a dose of 1 mg/kg apomorphine and then placed in an enclosed environment, such as an inverted wire cage, they are seen to climb around the walls. This behavioural phenomenon is thought to be a consequence of the stimulation of post-synaptic Dopamine (D.A.) receptors in the nucleus accumbens. Inhibition of apomorphine induced climbing is therefore indicative of post-synaptic D.A. receptor blockade in the accumbens.

Groups of 10 male CDI mice, weighing 25–30 g were pretreated orally with either graded doses of the test compound or vehicle, at appropriate time intervals before the subcutaneous administration of a sub-maximal dose of apomorphine (1 mg/kg). Immediately after the apomorphine injection the mice were placed in wire 'climbing cages' and each animal was scored for climbing behaviour at 10 and 20 minutes post apomorphine as follows:

Four paws on cage floor=0
Fore paws on cage wall=1
Four paws on cage wall=2

The total score was calculated for each group of mice and expressed as a percentage inhibition of climbing.

$$\% \text{ inhibition} = 100 - \frac{\text{Total score for test compound} \times 100}{\text{Total score for apomorphine control}}$$

ED50's and fiducial limits were calculated according to the method of Litchfield and Wilcoxon, the ED50 being the dose that produced a 50% inhibition of apomorphine-induced climbing.

The table shows the dose for 50% inhibition at ½ hour post dosing p.o.

| Compound of Example No. | $ED_{50}$ mg/kg p.o. |
|---|---|
| 2 (a) | 0.235 |
| 2 (b) | 0.195 |
| 2 (c) | 0.48 |
| 2 (d) | 0.52 |

Toxicity

No toxic effects were observed in the test reported above.

Pharmacological Data—Antihypertensive Activity

Systolic blood pressures were recorded by a modification of the tail cuff method described by I M Claxton, M G Palfreyman, R H Poyser, R L Whiting, European Journal of Pharmacology, 37, 179 (1976). W+W BP recoreder, model 8005, was used to display pulses prior to all measurements rats were placed in a heated environment (33.5+0.5° C.) before transfer to a restraining cage. Each determination of blood pressure was the mean of at least 6 readings. Spontaneously hypertensive rats (ages 12–18 weeks) with systolic blood pressures>170 mmHg were considered hypertensive.

| Compound | Time Post Dost Hours | % Change in Systolic blood pressure |
|---|---|---|
| (2 g) 10 mg/kg p.o. | 4 | −18 |
| (2 f) 10 mg/kg p.o. | 4 | −32 |

Toxicity

No toxic effects were observed in the test reported above.

I claim:

1. A compound of formula (I), or a pharmaceutically acceptable salt or N-oxide thereof; or a solvate of any of the foregoing:

(I)

wherein:
$R_1$ is $C_{1-6}$alkoxy, $C_{1-6}$alkylthio or, together with $R_5$ is $C_{1-2}$alkylene, and one of $R_2$, $R_3$ and $R_4$ is hydrogen and the other two together are $C_{1-2}$ alkylenedioxy, or the other two are the same or different and are selected from hydrogen, halogen, trifluoromethyl, $C_{1-6}$ alkyl, $C_{1-6}$ alkoxy, $C_{1-6}$ alkylthio, $C_{1-7}$acyl, $C_{1-7}$ acylamino, $C_{1-6}$alkylsulphonyl, $C_{1-6}$alkylsulphinyl hydroxy, nitro or amino, aminocarbonyl or aminosulphonyl optionally N-substituted by one or two $C_{1-6}$alkyl, $C_{3-8}$ cycloalkyl, phenyl or phen $C_{1-4}$alkyl groups or optionally N-disubstituted by $C_{4-5}$ polymethylene, or $R_1$ and $R_2$ together are $C_{1-2}$ alkylenedioxy, and $R_3$ and $R_4$ together are $C_{1-2}$ alkylenedioxy or $R_3$ and $R_4$ are the same or different and are selected from the previously defined class of substituents:
$R_5$ is hydrogen or as defined with $R_1$;
$R_6$ is hydrogen or $C_{1-6}$ alkyl; and
Ar is phenyl or thien-2-yl or thien-3-yl, optionally substituted by one or two groups, which are the same or different, selected from $C_{1-4}$ alkoxy, trifluoromethyl, halogen, carboxy, esterified carboxy or $C_{1-4}$ alkyl optionally substituted by hydroxy, $C_{1-4}$alkoxy, carboxy, esterified carboxy or in vivo hydrolysable $C_{1-4}$acyloxy; Ar being in the 3β configuration as defined in formula (VIII)

(VIII)

and Ar may also have the 3α-configuration either when one of $R_2$, $R_3$ and $R_4$ is hydrogen and the other two are independently selected from optionally substituted amino or aminosulphonyl as defined, $C_{1-6}$ alkylsulphonyl or $C_{1-6}$ alkylsulphinyl; or when $R_1$ and $R_2$ together are $C_{1-2}$ alkylenedioxy and $R_3$ and $R_4$ are independently selected from the same group of substituents.

2. A compound according to claim 1 of formula (III), or a pharmaceutically acceptable salt thereof or a solvate of either of the foregoing:

(III)

wherein $R_1'$ is $C_{1-6}$alkoxy and one of $R_2'$, $R_3'$ and $R_4'$ is hydrogen and the other two are the same or different and are each hydrogen halogen, hydroxy, $C_{1-6}$alkoxy, $C_{1-6}$alkylthio, trifluoromethyl, amino or $C_{1-4}$alkanoylamino and $R_6$ and Ar are as defined in claim 1.

3. A compound according to claim 2, wherein
$R_1'$ is methoxy, $R_2'$ is hydrogen, $R_3'$ is amino or $C_{1-4}$alkanoylamino and $R_4'$ is chloro.

4. A compound according to claim 1 of formula (IV), or a pharmaceutically acceptable salt or N-oxide thereof; or solvate of any of the foregoing:

(IV)

wherein $R_1''$ is $C_{1-6}$alkoxy, one of $R_2''$ $R_3''$ and $R_4''$ is hydrogen and the other two are the same or different and are selected from hydrogen, $C_{1-6}$alkylsulphonyl, $C_{1-6}$alkylsulphinyl or amino or aminosulphonyl optionally N-substituted by one or two $C_{1-6}$alkyl groups, or $R_1''$ and $R_2''$ together are methylenedioxy or ethylenedioxy and $R_3''$ and $R_4''$ are the same or different and are selected from the previously defined class of substituents, and $R_6$ and Ar are as defined hereinbefoe and Ar is in the β-configuration.

5. A compound according to claim 4, wherein neither of the other two of $R_2''$, $R_3''$ and $R_4''$ is hydrogen, so that Ar may also be in the α-conformation.

6. A compound according to any one of claims 2 to 5 wherein Ar is phenyl mono-substitued in the para-position by chloro, fluoro or methyl, or in the ortho-position by fluoro.

7. A compound according to claim 6 which is
4-amino-5-chloro-2-methoxy-N-[7′β-(3′β-p-fluorophenyl-1′-aza-5′αH-bicyclo[4,3,0]nonyl)-]benzamide,
4-amino-5-chloro-2-methoxy-N-[7′β-(3′β-o-fluorophenyl-1′-aza-5′αH-bicyclo[4,3,0]nonyl)-]benzamide
a pharmaceutically acceptable acid addition salt thereof or a solvate of either of the foregoing.

8. A compound according to claim 6 which is
4-amino-5-methylsulphonyl-2-methoxy-N-[7′β-(3′β-p-fluorophenyl-1′-aza-5′αH-bicyclo[4,3,0]nonyl)-]benzamide
a pharmaceutically acceptable salt or N-oxide thereof or a solvate of any of the foregoing.

9. A compound according to any one of claims 2 to 5 wherein Ar is unsubstituted phenyl.

10. A compound according to claim 9 which is
4-amino-5-chloro-2-methoxy-N-[7'β-(3'β-phenyl-1'-aza-5'αH bicyclo{4,3,0}nonyl)}benzamide,
4-amino-5-chloro-2-methoxy-N-[7'β-(3'α-methyl-3'β-phenyl-1'-aza-5'αH-bicyclo[4,3,0]nonyl)]benzamide,
a pharmaceutically acceptable acid addition salt thereof, a solvate of either of the foregoing.

11. A compound according to claim 9 which is
4-amino-5-methylsulphonyl-2-methoxy-N-[7'β-(3'β-phenyl-1'-aza-5'αH-bicyclo[4,3,0]nonyl)]benzamide,
4-amino-5-methylsulphonyl-2-methoxy-N-[7'β-(3'α-phenyl-1'-aza-5'αH-bicyclo[4,3,0]nonyl)]benzamide,
or a pharmaceutically acceptable salt or N-oxide thereof or a solvate of any of the foregoing.

12. A compound according to claim 1 of formula (IV), or a pharmaceutically acceptable solvate or N-oxide thereof, or solvate of any of the foregoing:

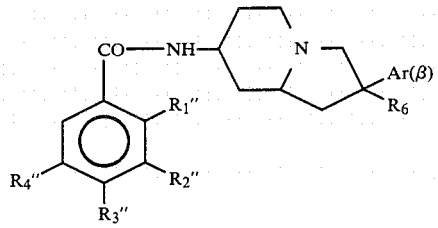

(IV)

wherein $R_1''$ is $C_{1-6}$ alkoxy, one of $R_2''$ $R_3''$ and $R_4''$ is hydrogen and the other two are the same or different and are selected from $C_{1-6}$ alkylsulphonyl, $C_{1-6}$ alkylsulphinyl or amino or aminosulphonyl optionally N-substituted by one or two $C_{1-6}$ alkyl groups, or $R_1''$ and $R_2''$ together are methylenedioxy or ethylenedioxy and $R_3''$ and $R_4''$ are the same or different and are selected from the previously defined class of substituents, and $R_6$ and Ar are as defined hereinbefoe and Ar is in the α-configuration.

13. A pharmaceutical composition comprising a pharmaceutically effective amount for the treatment of psychosis in mammals of a compound according to claim 1 or a pharmaceutically acceptable salt thereof, or N-oxide thereof or a solvate of any of the foregoing and a pharmaceutically acceptable carrier.

14. A method of treatment or prophylaxis of psychosis in mammals, such as humans, which comprises the administration of an effective amount of a compound according to claim 1, or a pharmaceutically acceptable acid addition salt thereof, or a solvate of either of the foregoing.

15. A method of treatment or prophylaxis of cardiac arrhythmia in mammals including humans, comprising the administration to a sufferer of a therapeutically effective amount of a compound according to claim 5, a pharmaceutically acceptable salt or an N-oxide thereof, or a solvate of any of the foregoing.

16. A method of treatment or prophylaxis of hypertension in mammals including humans, which comprises administering to the suffering mammal an anti-hypertensive effective amount of a compound according to claim 5, a pharmaceutically acceptable salt thereof, or an N-oxide thereof, or a solvate of any of the foregoing.

17. A compound of formula (XI):

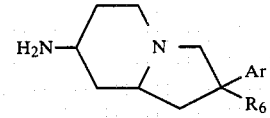

wherein $R_6$ and Ar are as defined in claim 1.

* * * * *